United States Patent [19]

Jäger et al.

[11] Patent Number: 5,468,352
[45] Date of Patent: Nov. 21, 1995

[54] PROCESS FOR PREPARING PERFLUOROPOLYETHERS

[75] Inventors: Gerhard Jäger, Heideweg; Hans Millauer, An den, both of Germany

[73] Assignee: Hoechst Aktiengesellschaft, Frankfurt am Main, Germany

[21] Appl. No.: 389,062

[22] Filed: Feb. 14, 1995

Related U.S. Application Data

[63] Continuation of Ser. No. 78,564, Jun. 17, 1993, abandoned.

[30] Foreign Application Priority Data

Jul. 1, 1992 [DE] Germany ............... 42 21 555.2

[51] Int. Cl.$^6$ .................................................. C25B 3/08
[52] U.S. Cl. ............................ 204/59 F; 204/81
[58] Field of Search ................... 204/72, 59 F, 81

[56] References Cited

U.S. PATENT DOCUMENTS 4,052,277  10/1977  Martini ............... 204/157.69

FOREIGN PATENT DOCUMENTS

| | | |
|---|---|---|
| 0619798 | 2/1992 | Australia . |
| 103334 | 6/1983 | Japan . |
| 61-21610 | 6/1983 | Japan . |
| WO91/15616 | 10/1991 | WIPO . |

OTHER PUBLICATIONS

Grinberg et al. Investigation of the Processes of Electrochemical Perfluoroalkylation and Fluorosulphation, Part I. Electrode Processes and the Electrochemical Perfluoroalkylation Mechanism, Journal of Electroanalytical Chemistry, vol. 325, Nos. 1 and 2, pp. 179–180 (Mar. 1992).

J. Electroanal. Chem., Bd. 325, Nr. 1–2 (Mar. 1992) pp. 167–184.

C.A. 113:86921 (Sep. 1990).

*Primary Examiner*—John Niebling
*Assistant Examiner*—Edna Wong
*Attorney, Agent, or Firm*—Connolly and Hutz

[57] ABSTRACT

Perfluoropolyethers of the formula

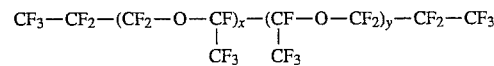

in which x and y are an integer from 1 to 4, can be obtained by electrolytic decarboxylation of perfluorocarboxylic acid of the formula

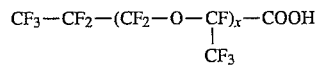

in which x is an integer from 1 to 4. The electrolytic decarboxylation is carried out in an aqueous electrolyte fluid in the presence of aliphatic nitrile having an alkyl radical of from 1 to 6 carbon atoms.

8 Claims, No Drawings

PROCESS FOR PREPARING PERFLUOROPOLYETHERS

This application is a continuation of application Ser. No. 08/078,564 filed on Jun. 17, 1993 now abandoned.

The present invention relates to a process for preparing perfluoropolyethers of the formula

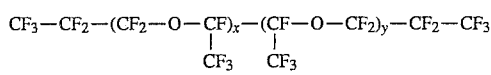

in which x and y are an integer from 1 to 4, by electrolytic decarboxylation of perfluorocarboxylic acid of the formula

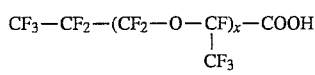

in which x is an integer from 1 to 4.

Perfluoropolyethers have excellent thermal stability and chemical stability, which make it possible to use these compounds in many different ways. Perfluoropolyethers can be heated to their boiling point of from 200° to 350° C. for long periods without decomposition. Even the presence of organic substances or molten metals, such as used in vapor solder baths for electronic components (vapor phase soldering) results in barely noticeable decomposition of the perfluoropolyethers. Furthermore, perfluoropolyethers, owing to their chemical resistance, can be used for checking out electronic components. In this context it is advantageous that these compounds are liquid over a wide temperature range. Typical check-out tests of electronic components are, for example, the "thermal shock test" the "gross leak test" and the "burn-in test" as described in EP-A-0,203,348.

Perfluoropolyethers are notable for high dielectric strength (>150 kV·cm$^{-1}$ at 20° C.), very low electric conductivity (<10$^{-9}$ S·cm$^{-1}$ at 25° C.) and a small dielectric constant (<2 at 25° C.). Perfluoropolyethers can therefore be used for cooling live electrical appliances. A further special property of perfluoropolyethers is their excellent solution power for oxygen and carbon dioxide. They can therefore be used as an oxygen carrier in heart-lung machines or directly as a blood substitute. Perfluoropolyethers can further be used as oxygen and carbon dioxide carriers for off-gas-free fermentation processes.

Perfluoropolyethers can be used as heat transfer media and as hydraulic fluids, and as lubricants under extreme chemical and thermal loads.

A number of processes for preparing perfluoropolyethers have been described before now.

U.S. Pat. No. 4,052,277 describes a photochemical process starting from perfluorinated carbonyl compounds which requires exposure times of from 10 to 20 hours and proceeds with low space-time yields.

A more economical route for preparing perfluoropolyethers is provided by the electrochemical coupling processes which are called Kolbe electrolyses. The preparation methods of this type described hitherto are distinguished by the use of aqueous-alcoholic electrolytes in which the perfluorocarboxylic acids used are dissolved in the form of its salts or as mixtures of salts and free acids.

Japanese Offenlegungsschrift Sho-58-103 334 describes the preparation of symmetric perfluoropolyethers with x=1 or 2, and of asymmetric perfluoropolyethers with x=1 and y=2. The perfluoropolyether yields are approximately from 37 to 64%. The process is carried out in polyalcoholic electrolytes.

EP-A-0,355,726 describes the preparation of symmetric and asymmetric perfluoropolyethers with x=1 to 4 and y=1 to 4. The polyfluoroether yields are from 77 to 88%, and the current yields are from 52 to 70%. The electrolyte used in the process is methanol or a methanol/water mixture.

WO 91/15616 describes the preparation of perfluoropolyethers, in which the electrolyte used is a water/methanol mixture. In this instance, the use of potassium, ammonium, rubidium or cesium salts of the perfluorocarboxylic acids is emphasized as being particularly advantageous in avoiding gel formation which would interfere with the electrolysis. The maximum yields of material attained are 82.5%, the current yields are around 40%.

The processes described hereinabove are not satisfactory with regard to the achievable product yields. This is true especially because the perfluorocarboxylic acids used are very expensive materials. The low current yields are a further drawback.

When methanolic electrolytes are used, by-products are formed according to the following reactions:

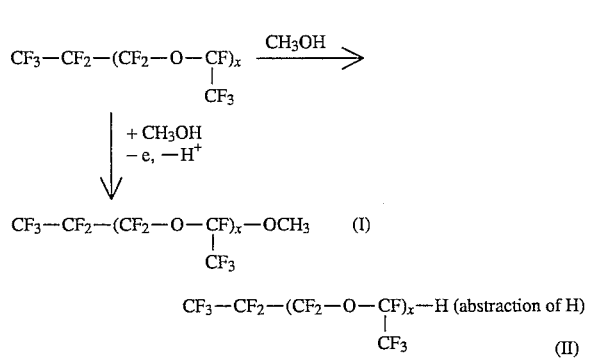

The radical formed as an intermediary in the Kolbe electrolysis forms the by-product (II) by abstraction of hydrogen from the methanol. Further oxidation of the radical formed as an intermediary, followed by saturation with methanol, produces the by-product (I) in an amount of from 3 to 6% by weight.

If conventional purification processes such as extraction or fractional distillation are used, the by-products of the formula (I) cannot be separated or cannot be separated sufficiently completely as to achieve the high purities of >99.9% demanded for perfluoropolyethers. In these cases it is therefore necessary to carry out additional, laborious purification operations. AU-619 798 B2 describes a process for pyrolytic purification of perfluoropolyethers, in which the impure perfluoropolyether is passed over catalysts in vapor form at from 150° to 360° C. In this process, some of the perfluoropolyether is always destroyed at the same time.

The by-products of the formula (II) are formed in amounts of 1–2% and likewise impede purification of the perfluoropolyethers.

The object of the invention is therefore to provide a process for preparing perfluoropolyethers, in which perfluorocarboxylic acid is converted into perfluoropolyether with a high product yield and current yield, and the perfluoropolyether is obtained without an additional purification step in a purity of more than 99%.

It has been found, surprisingly, that this object can be achieved by an electrolytic decarboxylation of perfluorocarboxylic acid in an aqueous electrolyte fluid in the presence of aliphatic nitrile having an alkyl radical of from 1 to 6 carbon atoms.

The process according to the invention may optionally and preferably be distinguished in that 1) an aliphatic nitrile having from 1 to 4 carbon atoms is used;
2) the aliphatic nitrile used is acetonitrile, propionitrile or isobutyronitrile;
3) an aqueous electrolyte fluid is used comprising from 1 to 50, especially from 10 to 30, % by weight of aliphatic nitrile;
4) an electrolyte fluid is used comprising from 1 to 70, especially from 20 to 50, % by weight of perfluorocarboxylic acid;
5) the electrolytic decarboxylation is carried out at temperatures from $-10°$ C. to $90°$ C., especially at from $0°$ to $60°$ C.;
6) a current density of from 20 to 500, especially from 50 to 250, $mA/cm^2$ is set;
7) the perfluorocarboxylic acid is used in the form of its salts or in part-neutralized form, a degree of neutralization of from 5 to 100%, preferably of from 50 to 100%, being set;
8) salts of sodium, potassium, ammonium or tetraalkylammonium are used for salt formation;
9) during the electrolytic decarboxylation, more perfluorocarboxylic acid is metered in in proportion to the extent to which it is consumed in the process of electrolytic decarboxylation.

When preparing symmetric perfluoropolyethers, ie. the numerical values for x and y are identical, the perfluorocarboxylic acids which are subjected to electrolytic decarboxylation are composed of identical molecular chains, ie. the numerical value for x is the same for all molecules.

If perfluorocarboxylic acids having different numerical values for x are together subjected to electrolytic decarboxylation, this results in asymmetric perfluoroethers mixed with the symmetric perfluoroethers according to the following scheme:

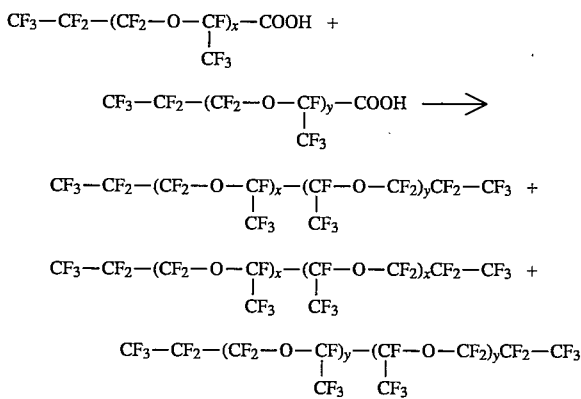

Using the process according to the invention, product yields of more than 95 to 98%, based on the reacted perfluorocarboxylic acid, are achieved. If the proportion of nitrile in the electrolyte fluid is 33% by weight, a current yield of 90 to 97% is achieved.

In the process according to the invention it is not necessary to choose a particularly high proportion of the nitrile used. Whilst, as shown in Comparative Example 1, in the absence of acetonitrile virtually no perfluoropolyethers are formed, the product yield with a proportion of 4 percent by weight of acetonitrile in the electrolyte fluid (Example 2) is 95.4% and the current yield is 71.5%. An increase of the acetonitrile proportion (Examples 3 and 4) results in only slight further yield improvements.

If water/nitrile mixtures are used, the crude products which can be isolated from the electrolyte fluid already have a purity of >99%, usually even as high as 99.8% of perfluoropolyethers. This makes the purification operations considerably simpler.

The electrolysis can in principle be carried out in any vessel suitable for electrolysis, for example in simple beaker cells or in flow cells.

It is usually sufficient to use an undivided electrolytic cell. Alternatively, however, a subdivided cell may be used whose anolyte and catholyte compartments are separated from one another by a membrane or a diaphragm.

The electrodes used can be made of the conventional materials for Kolbe electrolysis. For the anode, platinum or other noble metals, metals coated with platinum or other noble metals, and vitreous carbon are preferred. Preferred as cathode material are graphite and stainless steels.

The following examples are intended to explain the process according to the invention in more detail.

EXAMPLES 1 TO 5

The electrolytic cell used comprises a cylindrical glass vessel (height 150 mm, internal diameter 70 mm) which is provided with a cooling jacket and a drain cock at the bottom. The anode used is a platinum sheet (width 55 mm, height 110 mm); the cathode employed is a wide-mesh stainless-steel netting (width 55 mm, height 110 mm; mesh size 2 mm, wire thickness 1 mm). The electrodes are arranged parallel to one another at a mutual distance of 5 mm and are attached vertically to a polyethylene holder on the removable cell cover. The electrode area immersed into the electrolyte is approximately 35 $cm^2$. The electrolyte is agitated by means of a magnetic stirrer (length 55 mm).

In each case, 20.0 g (0.50 mol) of sodium hydroxide are dissolved in m grams of water, to which solution 246 g (0.50 mol) of perfluoro-2,5-dimethyl-3,6-dioxanonanoic acid [x=2] are added with shaking, followed by the addition of n grams of the nitrile. Electrolysis of the solution obtained is carried out in each case at a temperature of $40°$ C. and a current of 2.70 ampere to a charge throughput of 21.4 ampere-hours. The cell voltage is 5.5–6 volts. By adding further acid from a dropping funnel, the pH of the electrolyte fluid is kept between 4 and 6 during the electrolysis. The greater part of the crude product separates as a heavy phase from the electrolyte fluid and can be drained at the bottom of the cell. After completion of the electrolysis, the electrolyte fluid present at a pH of 7 is extracted 3 times with 100 ml portions of 1,1,2-trichloro-1,2,2-trifluoroethane. The electrolyte fluid is then acidified with 150 g of 50% strength sulfuric acid, and the unreacted perfluorocarboxylic acid is separated as the heavy phase and recovered. The acid content of the phase obtained as above is determined by titration with 1N NaOH. From the difference between the amounts of acid used and acid recovered, the acid consumption (p grams) is obtained. The combined 1,1,2-trichloro-1,2,2-trifluoroethane extracts are freed of the extractant by distillation, the residue is combined with the bulk of the raw product and is extracted with 100 ml of 1M aqueous sodium hydroxide. The amount and the composition, determined by gas chromatography, of the crude perfluoropolyether present after extraction with aqueous sodium hydroxide, and the yields obtained are shown in the following table:

| Ex. No. | H₂O m(g) | Nitrile n(g) | Acid consumption p(g) | Perfluoropolyether crude product Amount (g) | Perfluoropolyether crude product Content (%) | Product yield (%)[a] | Current yield (%) |
|---|---|---|---|---|---|---|---|
| 1[b] | 250 | without | — | — | — | <1 | <1 |
| 2 | 240 | 10 acetonitrile | 298.9 | 258.2 | >99.8 | 95.4 | 71.5 |
| 3 | 235 | 15 acetonitrile | 321.2 | 276.0 | >99.8 | 94.4 | 76 |
| 4 | 225 | 25 acetonitrile | 324 | 286 | >99.8 | 96.6 | 79 |
| 5 | 240 | 10 propionitrile | 238.4 | 197.9 | >99.8 | 91.3 | 55 |

[a] The product yield is based on the acid consumed
[b] Example 1 is a comparative example not according to the invention

EXAMPLE 6

An electrolytic cell is used as described in Examples 1 to 5; instead of platinum, the anode used is a plate of vitreous carbon (Sigradur K®; width 55 mm, height 110 mm, thickness 4 mm).

A solution of 10.0 g (0.25 mol) of sodium hydroxide in 250 g of water is admixed, with shaking, with 165 g (approx. 0.255 mol) of a mixture comprising 93% perfluoro-2,5,8-trimethyl-3,6,9-trioxadodecanoic acid [x=3] and 7% perfluoro-2,5-dimethyl-3,6-dioxanonanoic acid [x=2], and 125 g of acetonitrile are added to the electrolyte fluid obtained. Electrolysis is carried out at a temperature of 40° C., a current of 2.7 ampere and a cell voltage of from 7 to 8 volt up to an electric charge of 18.1 ampere-hours. As the electrolysis proceeds, the pH of the electrolyte is kept between 4 and 7 by the addition of a further 301 g (0.465 mol) of the acid mixture described above from a dropping funnel. The greater part of the crude product, approximately 360 g, separates from the electrolyte fluid as a heavy phase and is drained at the bottom of the cell. After completion of the electrolysis, the electrolyte fluid present at a pH of 7 is extracted 3 times with 100 ml portions of 1,1,2-trichloro-1,2,2-trifluoroethane. The residue remaining after the solvent has been distilled off is combined with the bulk of the crude product and washed with 100 ml of 1M aqueous sodium hydroxide. The amount of crude perfluoropolyether mixture obtained is 367.5 g. By mixing the electrolyte fluid with 150 g of 50% strength sulfuric acid and separating the phases, 154 g (0.238 mol) of the perfluorocarboxylic acid mixture used as starting material are recovered, which still contain some water and acetonitrile.

Gas-chromatographic analysis of the product mixture gives a 99.8% proportion of perfluoropolyethers of the following composition:

| perfluoropolyethers with x = 2 | 0.6% by wt. |
| perfluoropolyethers with x = 3 | 83.2% by wt. |
| perfluoropolyethers with x = 2 and y = 3 | 16.0% by wt. |

The product yield of perfluoropolyethers overall is 98.3%, based on the acid consumed; the current yield is 90.5%.

EXAMPLE 7

An electrolytic cell is used as described in Example 6.

A solution of 8.0 g (0.20 mol) of sodium hydroxide in 250 g of water is admixed, with shaking, with 166 g (approx. 0.20 mol) of perfluoro-2,5,8,11-tetramethyl- 3,6,9,12-tetraoxapentadecanoic acid [x=4] and 100 g of propionitrile are added. The mixture obtained is electrolyzed at a temperature of 40° C., a current of 2.7 ampere and a cell voltage of from 9–11 volt up to an electric charge of 15.4 ampere-hours. As the electrolysis proceeds, the pH of the electrolyte is kept between 4 and 7 by the addition of a further 362 g (0.437 mol) of the acid.

After completion of the electrolysis, the crude product is separated from the electrolyte in a separating funnel and washed twice with 1000 ml of 1M aqueous sodium hydroxide. The amount of crude perfluoropolyether is 312.9 g; gas-chromatographic analysis of the product gives a proportion of 99.6% of perfluoropolyethers having the following composition:

| perfluoropolyethers with x = 3 and y = 4 | 0.8% by wt. |
| perfluoropolyethers with x = 4 | 98.8% by wt. |

By mixing the electrolyte with 150 g of 50% strength sulfuric acid and separating the phases obtained, 191.3 g (0.231 mol) of the acid used are recovered.

The product yield of perfluoropolyethers overall is 98.0%, based on the acid consumed; the current yield is 69.3%.

EXAMPLE 8

An undivided flow cell having plate-shaped electrodes arranged in parallel with an electrode area of 200 cm² each is used. The anode is made of vitreous carbon (Sigradur K®), the cathode is made of high-grade steel. The electrode gap is 1 mm.

The electrolyte circuit comprises a centrifugal pump, the cell described above and an electrolyte holding vessel made of glass which is provided with a cooling coil. The filling volume of the apparatus is approximately 2.5 l. On the lowest point of the apparatus there is a glass nozzle with a valve for draining the separated crude product.

80 g (2.0 mol) of sodium hydroxide are dissolved in 1000 g of water, and 1000 g (2.02 mol) of perfluoro-2,5-dimethyl-3,6-dioxanonanoic acid [x=2] are added with slow pumped circulation. The solution is set to a pH of 4–5 and admixed with 500 g of acetonitrile.

The electrolysis fluid is electrolyzed at a temperature of 40°–45° C., a current of 16 ampere and a voltage of 5.3–5.5 volt. The pumpover rate is approximately 400 l/h. The pH of the electrolysis fluid is kept in the range of pH 4 to 5 by metering in further acid by means of a pH-controlled dosing pump.

The crude product separated during electrolysis is drained and collected at intervals. After 20 hours, corresponding to an electric charge of 320 ampere hours, the electrolysis is terminated. In total, 5840 g (11.77 mol) of acid are consumed, and 5247 g of crude product are separated. The crude product is transferred into a 6 l glass flask equipped with a precision glass stirrer and a bottom drain cock and is washed by stirring with 1000 ml of 2N aqueous sodium hydroxide. After phase separation, 5233 g of crude perfluoropolyether are obtained. By means of gas chromatography, a 99.8% proportion of perfluoropolyether in the crude product is determined. Of this, 99.3% by weight relates to the compound with x=2, and 0.5% by weight to the compound with x=2 and y=1.

The product yield of perfluoropolyethers is 98.5%, based on the acid consumed; the current yield is 97%.

By acidifying the electrolyte with 50% strength sulfuric acid, the unreacted starting acid can be recovered and reused for the next electrolysis batch. The aqueous sodium hydroxide used for extraction can likewise be used for the electrolyte of the next batch.

EXAMPLE 9

An electrolysis apparatus is used as described in Example 8.

80 g (2.0 mol) of sodium hydroxide are dissolved in 1000 g of water and admixed, while pumping over slowly, a mixture comprising 330 g (1.0 mol) of perfluoro-2-methyl-3-oxahexanoic acid [x=1] and 662 g (1.0 mol) of perfluoro-2,5,8-trimethyl-3,6,9-trioxadodecanoic acid [x=3]; the solution obtained is set to a pH of 4–5 and admixed with 500 g of acetonitrile.

The electrolysis fluid is electrolyzed at a temperature of 40°–45° C., a current of 16 ampere and a voltage of 5.3–5.4 volt. The pumpover rate is approximately 400 l/h. The pH of the electrolysis fluid is kept in the range of pH 4.5 to 5.5 by metering in further acid mixture of the abovementioned composition by means of a pH-controlled dosing pump.

The crude product separated during electrolysis is drained and collected at intervals. After 10 hours, corresponding to an electric charge of 160 ampere-hours, the electrolysis is terminated. A total of 2648 g of crude product were separated. In total, 2720 g (5.48 mol) of acid were consumed. The crude product is transferred into a stirred glass flask equipped with a bottom drain cock and is washed by stirring with 1000 ml of 2N aqueous sodium hydroxide. After phase separation, 2553 g (5.335 mol) of crude perfluoropolyether are obtained. The product mixture analyzed by gas chromatography comprises to 99.7% perfluoropolyethers of the following composition:

| | |
|---|---|
| Perfluoropolyether with x = 1 | 10.0% by wt. |
| Perfluoropolyether with y = 3 | 41.6% by wt. |
| Perfluoropolyether with x = 1 and y = 2 | 0.2% by wt. |
| Perfluoropolyether with x = 1 and y = 3 | 47.5% by wt. |
| Perfluoropolyether with x = 2 and y = 3 | 0.4% by wt. |

The product yield of perfluoropolyethers is 97.3% in total, based on the acid consumed; the current yield is 89.4%.

EXAMPLE 10

An electrolytic cell is used as described in Example 6. A solution of 20 g (0.50 mol) of sodium hydroxide in 225 g of water is admixed, with shaking, with 165 g (0.50 mol) of perfluoro-2-methyl-3-oxahexanoic acid (x=1) and then 25 g of isobutyronitrile are added. The solution obtained is electrolyzed at a temperature of 40° C., a current of 2.7 ampere and a cell voltage of 7 volts. As the electrolysis proceeds, the pH of the electrolyte is kept between 4 and 7 by the addition of 255 g of starting acid. The total electric charge is 23.2 ampere-hours.

166.7 g of crude product separate from the electrolyte; by extracting the electrolyte three times with 100 ml portions of 1,1,2-trichloro-1,2,2-trifluoroethane and distilling off the extractant, a further 60.5 g of crude product are obtained. After washing the combined crude products with 100 ml of 1N aqueous sodium hydroxide, a total of 226 g of product remain having a proportion, determined by gas chromatography, of 99.4% of perfluoropolyether with x=1.

By acidification of the electrolyte with sulfuric acid, repeated extraction with 1,1,2-trichloro-1,2,2-trifluoroethane and subsequent evaporation of the extractant, 140 g of starting acid are recovered.

The product yield of perfluoropolyethers is 92.5%, based on the acid consumed; the current yield is 91%.

We claim:

1. A process for preparing perfluoropolyethers of the formula

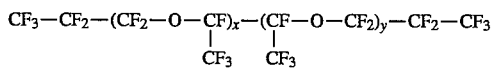

in which x and y are an integer from 1 to 4, by electrolytic decarboxylation of perfluorocarboxylic acid of the formula

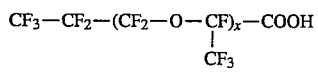

in which x is an integer from 1 to 4, which comprises carrying out the electrolytic decarboxylation at temperatures from −10° to 90° C. in an aqueous electrolyte fluid consisting essentially of from 1 to 50% by weight of aliphatic nitrile having an alkyl radical of from 1 to 6 carbon atoms and from 20 to 50% by weight of perfluorocarboxylic acid, and wherein during the electrolytic decarboxylation, more perfluorocarboxylic acid is metered in proportional to the extent to which it is consumed by the process of electrolytic decarboxylation.

2. The process as claimed in claim 1, wherein the aliphatic nitrile has 1 to 4 carbon atoms.

3. The process as claimed in claim 1, wherein the aliphatic nitrile is selected from the group consisting of acetonitrile, propionitrile and isobutyronitrile.

4. The process as claimed in claim 1, wherein a current density of from 20 to 500 mA/cm$^2$ is set.

5. The process as claimed in claim 1, wherein the perfluorocarboxylic acid is in the form of its salts or in part-neutralized form, a degree of neutralization of from 5 to 100% being set.

6. The process as claimed in claim 1, wherein salts of sodium, potassium, ammonium or tetraalkylammonium are used for salt formation.

7. The process of claim 1 which is free of additional purification steps.

8. The process of claim 1, wherein the electrolytic decarboxylation is carried out at a temperature of 40°–45° C.

* * * * *